United States Patent [19]

Deavenport et al.

[11] 4,346,248

[45] Aug. 24, 1982

[54] PREPARATION OF 2,4,5-TRICHLOROPHENOL AND 2,4,5-TRICHLOROPHENOXYACETIC ACID FREE OF 2,3,7,8-TETRACHLORO-DIBENZO-P-DIOXIN CONTAMINATION

[75] Inventors: Dennis L. Deavenport, Memphis, Tenn.; Kenneth J. Howard, North Little Rock; Albert E. Sidwell, Jacksonville, both of Ark.

[73] Assignee: Vertac Chemical Corporation, Memphis, Tenn.

[21] Appl. No.: 266,479

[22] Filed: May 22, 1981

Related U.S. Application Data

[63] Continuation of Ser. No. 122,838, Feb. 20, 1980, abandoned.

[51] Int. Cl.$^3$ ............................................. C07C 39/32
[52] U.S. Cl. ................................. 568/776; 568/774
[58] Field of Search .............................. 568/776, 774

[56] References Cited

U.S. PATENT DOCUMENTS 3,914,325 10/1975 Gavin et al. .................... 568/774
3,919,332 11/1975 Wollensak ...................... 568/774
4,216,342 8/1980 Virgilio et al. .................. 568/776

FOREIGN PATENT DOCUMENTS 2509407 11/1975 Fed. Rep. of Germany ...... 568/776
2373 6/1979 European Pat. Off. ............ 568/776

*Primary Examiner*—Werren B. Lone
*Attorney, Agent, or Firm*—Hammond & Littell, Weissenberger and Muserlian

[57] ABSTRACT

A process for the preparation of 2,4,5-trichlorophenol and 2,4,5-trichlorophenoxyacetic acid free of 2,3,7,8-tetrachloro-dibenzo-p-dioxin contamination by the steps of nitrating 1,2,4-trichlorobenzene, reducing the resulting 1,2,4-trichloro-5-nitrobenzene, diazotizing the resulting 2,4,5-trichloroaniline, hydrolyzing the resulting 2,4,5-trichlorobenzenediazonium salt and recovering 2,4,5-trichlorophenol. The 2,4,5-trichlorophenol is reacted with monochloroacetic acid to give 2,4,5-trichlorophenoxyacetic acid. Both the 2,4,5-trichlorophenol and the 2,4,5-trichlorophenoxyacetic acid produced by the process are analytically free of 2,3,7,8-tetrachloro-dibenzo-p-dioxin in analytical tests sensitive to 1 part per billion.

3 Claims, No Drawings

PREPARATION OF 2,4,5-TRICHLOROPHENOL AND 2,4,5-TRICHLOROPHENOXYACETIC ACID FREE OF 2,3,7,8-TETRACHLORO-DIBENZO-P-DIOXIN CONTAMINATION

This is a continuation of Ser. No. 122,838, filed Feb. 20, 1980, and now abandoned.

BACKGROUND OF THE INVENTION

This invention relates to a process for the synthesis of 2,4,5-trichlorophenol and 2,4,5-trichlorophenoxyacetic acid analytically free of 2,3,7,8-tetrachloro-dibenzo-p-dioxin in analytical tests sensitive to 1 part per billion.

The presently employed technology to produce 2,4,5-trichlorophenoxyacetic acid (2,4,5-T) and 2,4,5-trichlorophenol (2,4,5-TCP) commercially involves the declorination of 1,2,4,5-tetrachlorobenzene with aqueous sodium hydroxide or anhydrous sodium hydroxide in the presence of alcohols under elevated temperatures and pressures to form 2,4,5-TCP according to the flow diagram:

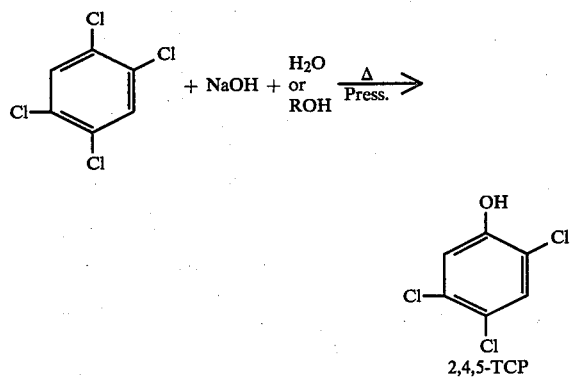

Under the conditions of alkalinity, temperature and pressure this process produces between 1 to 100 parts per million of the highly toxic teratogen 2,3,7,8-tetrachloro-dibenzo-p-dioxin (TCDD) according to the reaction:

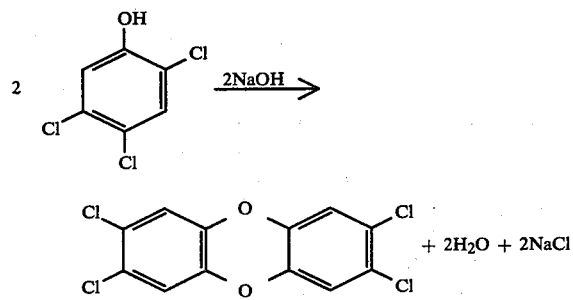

In the production of 2,4,5-TCP by this process, the TCDD produced is usually separated by careful distillation or by adsorption on activated carbon. However, the TCDD is claimed to be extremely toxic and cannot readily be disposed of. TCDD is a highly stable compound which is difficult to destroy chemically. Waste disposal by burying is difficult and unsatisfactory. Its destruction by incineration is a possibility which is presently being investigated. However, incineration of such a highly chlorinated compound is difficult and presents the possibility of contamination of either the scrubber liquor, the exhaust gas, or any solid residues.

The production of 2,4,5-T from 2,4,5-TCP is by reaction with monochloroacetic acid according to the reaction:

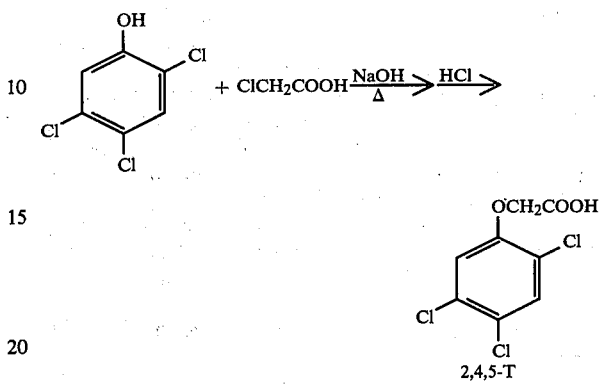

Conditions of this reaction are mild in comparison to the hydrolysis step to produce 2,4,5-TCP. Consequently, no measurable new formation of TCDD can be observed in the latter reaction.

OBJECTS OF THE INVENTION

An object of the present invention is the development of a process for the production of 2,4,5-trichlorophenol analytically free of 2,3,7,8-tetrachloro-dibenzo-p-dioxin, and its use in the production of 2,4,5-trichlorophenoxyacetic acid.

Another object of the present invention is the development of a process for the production of 2,4,5-trichlorophenol analytically free of 2,3,7,8-tetrachloro-dibenzo-p-dioxin consisting essentially of nitrating 1,2,4-trichlorobenzene in the presence of a strong mineral acid, reducing the resulting 1,2,4-trichloro-5-nitrobenzene, acidifying the resulting 2,4,5-trichloroaniline, diazotizing the resulting acid salt of 2,4,5-trichloroaniline, in the presence of a nitrite, hydrolytically decomposing the resulting 2,4,5-trichlorobenzenediazonium acid salt, and recovering 2,4,5-trichlorophenol analytically free of 2,3,7,8-tetrachlorodibenzo-p-dioxin in an analytical test sensitive to 100 part per billion.

A further object of the invention is the production of 2,4,5-trichlorophenoxyacetic acid analytically free of 2,3,7,8-tetrachloro-dibenzo-p-dioxin by reacting the above 2,4,5-trichlorophenol with monocholoroacetic acid in the presence of a base and acidifying the resulting salt.

These and other objects of the invention will become more apparent as the description thereof proceeds.

DESCRIPTION OF THE INVENTION

The above objects have been achieved by the synthesis of 2,4,5-trichlorophenoxyacetic acid and its intermediate, 2,4,5-trichlorophenol, which are free from contamination with 2,3,7,8-tetrachloro-dibenzo-p-dioxin (TCDD). The synthesis involves the nitration of 1,2,4-trichlorobenzene to form 1,2,4-trichloro-5-nitrobenzene, which is reduced (usually with hydrogen) to produce 2,4,5-trichloroaniline. The 2,4,5-trichloroaniline is reacted with sulfuric acid and a nitrite to form 2,4,5-trichlorobenzenediazonium sulfate, which is reacted with water and distilled to produce 2,4,5-trichlorophenol which is analytically free of TCDD. The 2,4,5-trichlorophenol is reacted with monochloroacetic acid in the presence of aqueous base, followed by acidification, to produce 2,4,5-trichlorophenoxyacetic acid which also is analytically free of TCDD.

More particularly, the invention relates to a process for the production of 2,4,5-trichlorophenol analytically free of 2,3,7,8-tetrachloro-dibenzo-p-dioxin consisting essentially of nitrating 1,2,4-trichlorobenzene in the presence of a strong mineral acid, reducing the resulting 1,2,4-trichloro-5-nitrobenzene, acidifying the resulting 2,4,5-trichloroaniline, diazotizing the resulting acid salt of 2,4,5-trichloroaniline, in the presence of a nitrite, hydrolytically decomposing the resulting 2,4,5-trichlorobenzenediazonium acid salt, and recovering 2,4,5-trichlorophenol analytically free of 2,3,7,8-tetrachlorodibenzo-p-dioxin in an analytical test sensitive to 1 part per billion.

The process of the invention follows the flow diagrams:

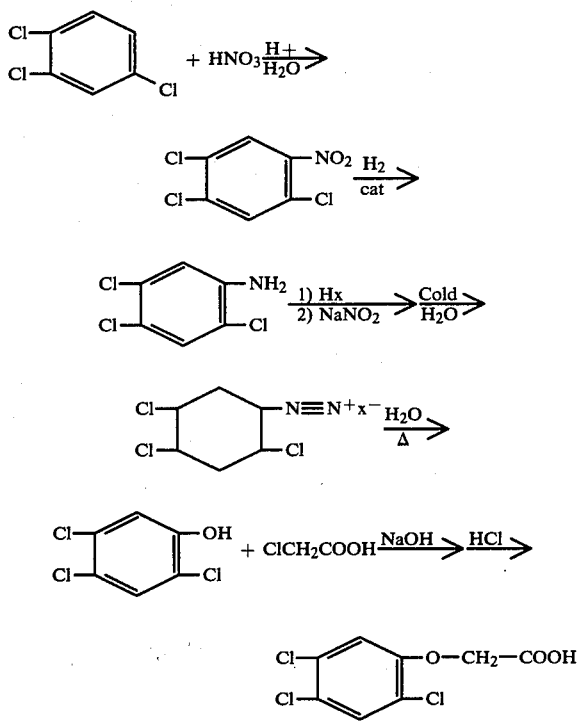

The starting material, 1,2,4-trichlorobenzene, is readily available. In the first stage, 1,2,4-trichlorobenzene is reacted with a nitrating agent under nitrating conditions. Conventional nitrating agents can be employed such as fuming nitric acid, preferably 90% fuming nitric acid, at a temperature of from 30° C. to 55° C., preferably 35° C. to 45° C., or mixed concentrated sulfuric acid/concentrated nitric acid at a temperature of from 60° C. to 100° C., preferably 70° C. to 90° C., or by reacting first with concentrated sulfuric acid at a temperature of from 50° C. to 100° C., preferably 60° C. to 90° C., and then with concentrated nitric acid at the same temperatures. The 1,2,4-trichloro-5-nitrobenzene is recovered by adding the reaction mixture to water, separating and washing the organic layer with water until the wash waters are neutral, or by cooling to below 10° C. and filtering.

In the second stage, the 1,2,4-trichloro-5-nitrobenzene is reduced under conditions reducing the nitro group to the amino group. Conventional reducing processes are employed such as catalytic hydrogenation or in situ hydrogenation by the action of an acid on a metal with formation of nascent hydrogen. Preferably catalytic hydrogenation is conducted in the presence or absence of an inert organic solvent at temperatures of 80° C. to 130° C., preferably 90° C. to 100° C. and hydrogen pressures of 75 to 250 psig, preferably 100 to 200 psig. Any hydrogenation catalysts capable of reducing nitro-groups to amines can be employed and a noble metal finely deposited on a carrier, such as platinum or palladium on charcoal or carbon, is preferred. If hydrogenation is effected by nascent hydrogen, a strong mineral acid such as hydrochloric acid is reacted with a heavy metal such as iron in an inert organic solvent such as ethanol up to the reflux temperature. The 2,4,5-trichloroaniline is worked up by filtration to remove the catalyst or heavy metal and the solvent is removed.

In the third stage, the 2,4,5-trichloroaniline is acidified with a strong mineral acid and the aniline salt is diazotized by the action of a nitrite, preferably an alkali-metal nitrite such as sodium nitrite, while suspended in a cold aqueous strong mineral acid solution at a temperature of below 10° C., preferably at a temperature from −5° C. to +5° C. Preferably the strong mineral acid is sulfuric or phosphoric acid. The 2,4,5-trichlorobenzenediazonium strong mineral acid salt in solution is filtered and utilized as such in the next stage.

In the fourth stage, the 2,4,5-trichlorobenzenediazonium strong mineral acid salt in solution in water is hydrolytically decomposed at a temperature from the reflux temperature to a temperature of 375° C. At the lower temperatures, the solution is refluxed in the presence of a cupric salt, the 2,4,5-trichlorophenol formed is steam distilled from the reaction and separately recovered. At higher temperatures of 130° C. to 375° C., preferably from 140° C. to 220° C., the aqueous solution is injected into a column packed with a suitable inert material and maintained at the desired temperature, either with or without additional super-heated steam. The 2,4,5-trichlorophenol steam distills from the top of the heated column and the concentrated aqueous strong mineral acid is recovered from the bottom of the column.

The 2,4,5-trichlorophenol is recovered with a purity of from 83% to 96% and no detectable amounts of 2,3,7,8-tetrachloro-dibenzo-p-dioxin could be found therein by gas chromatographic-mass spectrometry analysis capable of detecting 1 part per billion. Overall yields of 2,4,5-TCP from the starting 1,2,4-trichlorobenzene amount to from 58% to 62% in laboratory batch operations. In commercial operation, yields of at least 70% can be expected.

The 2,4,5-trichlorophenol can be employed for the production of 2,4,5-trichlorophenoxyacetic acid or hexachlorophene or for other applications. Since TCDD is not produced by the synthesis, no expensive recovery and TCDD disposition steps are required.

The following examples are illustrative of the practice of the invention without being limitative in any respect.

EXAMPLE 1

Overall Production of 2,4,5-T by the Process of the Invention 2723 gm (15.0 mols) of 1,2,4-trichlorobenzene were added to 7350 gm (105 mols) of 90% fuming nitric acid at 40° C. over a 3 hour period. The reaction mixture was held at 40° C. for one hour and worked up by the addition of 3700 ml of $H_2O$ while maintaining a temperature of 55°-60° C., and separating the waste acid. Two additional washes with 2000 ml of hot (55° C.) water and 1000 ml of 10% sodium bicarbonate solution followed by a phase separation gave 3316 gm (14.64 mols) of crude 1,2,4-trichloro-5-nitrobenzene. An additional 33 gm product was recovered from the waste acid when cooled and filtered.

226.5 gm (1.0 mols) of 1,2,4-trichloronitrobenzene were dissolved in 226 gm of isopropanol and hydrogenated in the presence of 6.1 gm of wet 1% Platinum on charcoal at 100° C. and 100-200 psig over a 90 minute period. The reaction mixture was filtered to remove the catalyst and the clear solution slowly dropped into a hot solution of 1125 gm of $H_2O$ and 500 gm of 98% sulfuric acid (5.0 mols) under vacuum to remove the isopropanol by distillation. The finely divided 2,4,5-trichloroaniline sulfate slurry was then cooled to −5° C. with good agitation and 56.9 gm (0.95 mols) of $NaNO_2$ in 125 ml of water were added over a 15 minute period while maintaining a maximum temperature of +5° C. After 30 minutes of agitation the reaction mixture was filtered to remove an insoluble impurity. The resulting 2,4,5-trichlorobenzenediazonium sulfate solution was then added cold (0°±5° C.) to a boiling solution of 1000 gm of cupric sulfate heptahydrate in 2000 ml of water. As the product is formed, it is removed from the zone of reaction by steam distillation. The product in the steam distillate is extracted with two 300 ml aliquots of methylene chloride and stripped to dryness to obtain 123 gm of crude 2,4,5-trichlorophenol (0.62 mol) which analyzed to be 95.1% pure.

This product, 123 gm (0.62 mol), was then added to a slurry of 72.7 gm (0.62 mol) of monochloroacetic acid in 190 ml toluene and 125 ml hydrocarbon solvent and reacted with 111.6 gm (1.4 mols) of 50% sodium hydroxide over a 10 minute period of time at 60°-92° C. After 15 minutes agitation the exothermic reaction was finished and 170 gm of 20% hydrochloric acid added to give a pH of less than 2.0. Another 31 gm of toluene were added at 80°-84° C. and the organic layer collected, cooled, filtered, washed with 30 ml of cold hydrocarbon solvent, and collected to give 85.6 gm (0.34 mol) of dry 2,4,5-trichlorophenoxyacetic acid (m.p.=149°-154° C).

Analysis of samples of the 2,4,5-trichlorophenoxyacetic acid and the intermediate 2,4,5-trichlorophenol by extractive work up and gas chromatographic-mass spectrometry analysis showed no trace contamination with 2,3,7,8-tetrachloro-dibenzo-p-dioxin at the one part per billion detection level.

EXAMPLE 2

Pyrolytic Decomposition of 2,4,5-Trichlorobenzenediazonium Sulfate to Produce TCDD Free 2,4,5-Trichlorophenoxy Acetic Acid The 2,4,5-trichlorobenzenediazonium sulfate solution (1.0 mol) prepared as indicated in Example 1, was injected cold into a preheated vertical column packed with a suitably inert material at temperatures between 140°-220° C. The partially vaporized material was forced through the heated zone rapidly with nitrogen. The crude condensate is then steam distilled to yield 140-165 gm of 2,4,5-trichlorophenol (83-94% purity). Analysis of this phenol and the corresponding 2,4,5-trichlorophenoxy acetic acid prepared as shown in Example 1 shows no TCDD at the 1 ppb detection limit.

EXAMPLE 3

Hydrolytic Decomposition of 2,4,5-Trichlorobenzenediazonium Sulfate to Produce TCDD Free 2,4,5-Trichlorophenoxy Acetic Acid 2,4,5-trichlorobenzenediazonium sulfate solution (1.0 mol) was injected into the center of a preheated packed column at temperatures between 140°-220° C. Superheated steam (230°-250° C.) was simultaneously injected with the feed stream as a carrier for the phenol produced during the pyrolysis of the diazonium solution. The waste acid solution was removed from the bottom of the column and the 2,4,5-trichlorophenol was recovered from the overhead condensate (145-170 gm of 2,4,5-trichlorophenol at 84-92% purity). Analysis of this phenol and the corresponding 2,4,5-trichlorophenoxy acetic acid prepared as shown in Example 1 shows no TCDD at the 1 ppb detection limit.

EXAMPLE 4

Nitration of 1,2,4-Trichlorobenzene with Mixed Sulfuric Acid/Nitric Acid

A mixture of 300 ml concentrated $H_2SO_4$ (98%) and 150 ml concentrated $HNO_3$ (90%) was prepared in a 2 liter flask equipped with an agitator, thermometer, and dropping funnel. A total of 90.8 gm of 1,2,4-trichlorobenzene (0.5 mol) was added to the acid mixture at 70°-90° C. over a 1 hour period of time. The reaction was maintained at this temperature for 2 to 3 hours or until analysis of the reaction mixture showed the reaction to be complete. Work-up of the product involved addition of 1 liter of cold water to the reaction mass while maintaining a temperature from 55°-65° C. Separation of the organic and aqueous layers gave the desired product, 1,2,4-trichloro-5-nitrobenzene. Crude yield is 95-98% of theory with an isomer purity of 91-95%. Subsequent reactions outlined in Example 1 show this material to be suitable for preparation of TCDD free 2,4,5-TCP and 2,4,5-T.

EXAMPLE 5

Nitration of 1,2,4-Trichlorobenzene by Sulfonation Followed by Nitration

A total of 90.8 gm of 1,2,4-trichlorobenzene (0.5 mol) was added to 370 ml of concentrated $H_2SO_4$ (98%) at 60°-90° C. and held with agitation for 45 minutes. To this reaction mixture, 200-300 ml of 90% $HNO_3$ were added dropwise until all of the starting material had reacted. The product was isolated by pouring over 2000 gm of cracked ice and filtering the resulting light yellow slurry. The crystals were washed with cold water until the filtrate was neutral to litmus. The yield is 93-95% of theory based on the crude dry product. The isomer purity of the product is 91-95% as 1,2,4-trichloro-5-nitrobenzene. Subsequent reactions outlined in Example 1 show this material to be suitable for preparation of TCDD free 2,4,5-TCP and 2,4,5-T.

EXAMPLE 6

Reduction of 1,2,4-Trichloro-5-nitrobenzene by the Iron/HCl Process

Into a flask equipped for efficient agitation and reflux was added 100 ml of 50% aqueous ethanol, 85 gm (1.5 mols) of iron filings, and a solution of 5.4 ml (0.06 mol) of concentrated HCl in 25 ml of ethanol. The flask was heated to reflux for 15 minutes while hydrogen was evolved from the surface of the iron. To the reaction mixture, a total of 113 gm (0.5 mol) of 1,2,4-trichloro-5-nitrobenzene was added dropwise (molten or dissolved in a minimum quantity of ethanol) over a period of 1 hour. The heat of reaction was removed by reflux cooling. While still hot, the reaction mass was vacuum filtered and the cake was washed with 50 ml of ethanol. The crude 2,4,5-trichloroaniline was recovered by stripping off the solvent under vacuum to give white to tan crystals in a crude yield of 96–98%. Purity ranged from 90–95% as the desired isomer. Subsequent reactions outlined in Example 1 show this material to be suitable for preparation of TCDD free 2,4,5-TCP and 2,4,5-T.

EXAMPLE 7

Reduction of 1,2,4-Trichloro-5-nitrobenzene by Hydrogenation in the Presence of 0.5–5% Pd on Carbon Catalyst A total of 113 gm (0.5 mol) of 1,2,4-trichloro-5-nitroaniline was placed in an autoclave with 200 ml of 95% ethanol and 2 gm of 1% Pd on carbon. The system was sealed and the temperature brought to 80°–100° C. Hydrogen was fed to the vessel at pressures varying between 100–200 psig until no further pressure drop was observed. The product was worked up by filtering to remove the catalyst and vacuum stripping to give an off-white product in 96–98% crude yield. Purity ranged from 88–94% as the desired isomer. Subsequent reactions outlined in Example 1 show this material to be suitable for preparation of TCDD free 2,4,5-TCP and 2,4,5-T.

EXAMPLE 8

Preparation of 2,4,5-T by Diazotization of 2,4,5-Trichloroaniline in Phosphoric Acid 226.5 gm (1.0 mol) of 1,2,4-trichloronitrobenzene were dissolved in 226 gm of isopropanol and hydrogenated in the presence of 6.1 gm of wet 1% Platinum on charcoal at 100° C. and 100–200 psig over a 90 minutes period. The reaction mixture was filtered to remove the catalyst and the clear solution was slowly dropped into a hot solution of 1125 gm of H$_2$O and 500 gm of phosphoric acid (5.0 mols) under vacuum to remove the isopropanol by distillation. The finely divided 2,4,5-trichloroaniline phosphate slurry was then cooled to $-5°$ C. with good agitation and 56.9 gm (0.95 mol) of NaNO$_2$ in 125 ml of water were added over a 15 minute period while maintaining a maximum temperature of $+5°$ C. After 30 minutes of agitation, the reaction mixture was filtered to remove an insoluble impurity. The resulting 2,4,5-trichlorobenzenediazonium phosphate solution was then added cold (0°±5° C.) to a boiling solution of 1000 gm of cupric sulfate heptahydrate in 2000 ml of water. As the product was formed, it was removed from the zone of reaction by steam distillation. The product in the steam distillate was extracted with two 300 ml aliquots of methylene chloride and stripped to dryness to obtain 115 gm of crude 2,4,5-trichlorophenol (0.58 mol) which analyzed to be 94.8% pure. This product was then added to a slurry of 68.0 gms (0.58 mol) of monochloroacetic acid in 190 ml of toluene and 125 ml of hydrocarbon solvent and reacted with 104.3 (1.31 moles) of 50% sodium hydroxide over a 10 minute period of time at 60°–92° C. After 15 minutes of agitation, the exothermic reaction was finished and 160 gm of a 20% hydrochloric acid solution were added to a pH of less than 2.0. Another 31 gm of toluene were added at 80°–84° C. and the organic layer was collected, cooled, filtered, washed with 30 ml of cold hydrocarbon solvent, and collected to give 80.0 gm (0.32 mol) of dry 2,4,5-trichlorophenoxyacetic acid (m.p.=148°–153° C.).

Analysis of samples of the 2,4,5-trichlorophenoxyacetic acid and the intermediate 2,4,5-trichlorophenol by extractive work up and gas chromatographic-mass spectrometry analysis showed no trace of contamination with 2,4,7,8-tetrachloro-dibenzo-p-dioxin at the one part per billion detection level.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the production of 2,4,5-trichlorophenol analytically free of 2,3,7,8-tetrachloro-dibenzo-p-dioxin consisting essentially of nitrating 1,2,4-trichlorobenzene with an acid selected from the group consisting of:
   (a) fuming nitric acid at a temperature of from 30° C. to 55° C.,
   (b) mixed concentrated sulfuric acid/concentrated nitric acid at a temperature of from 60° C. to 100° C. and
   (c) concentrated sulfuric acid at a temperature of from 50° C. to 100° C., followed by concentrated nitric acid at the same temperatures, reducing the resulting 1,2,4-trichloro-5-nitrobenzene by a process selected from the group consisting of catalytic hydrogenation and in situ hydrogenation by the action of an acid on a metal with formation of nascent hydrogen, acidifying the resulting 2,4,5-trichloroaniline with a strong mineral acid, diazotizing the resulting strong mineral acid salt of 2,4,5-trichloroaniline, in the presence of an alkali metal nitrite suspended in a cold aqueous strong mineral acid solution at a temperature below 10° C., hydrolytically decomposing the resulting 2,4,5-trichlorobenzenediazonium acid salt, in the presence of water or steam at a temperature of from reflux temperature to 375° C. and recovering 2,4,5-trichlorophenol analytically free of 2,3,7,8-tetrachloro-dibenzo-p-dioxin in an analytical test sensitive to 100 parts per billion.

2. The process of claim 1 wherein said decomposing step is conducted at the reflux temperature in the presence of a cupric salt.

3. The process of claim 1 wherein said decomposing step is conducted at a temperature of from 130° C. to 250° C. by injecting an aqueous solution of said diazonium acid salt into a column packed with a suitable inert material.

* * * * *